US009457089B2

(12) United States Patent
Soula

(10) Patent No.: US 9,457,089 B2
(45) Date of Patent: Oct. 4, 2016

(54) HIGHLY CONCENTRATED AQUEOUS PROTEIN SOLUTION WITH REDUCED VISCOSITY

(71) Applicant: ADOCIA, Lyons (FR)

(72) Inventor: Olivier Soula, Meyzieu (FR)

(73) Assignee: ADOCIA, Lyons (FR)

( * ) Notice: Subject to any disclaimer, the term of this patent is extended or adjusted under 35 U.S.C. 154(b) by 268 days.

(21) Appl. No.: 14/022,814

(22) Filed: Sep. 10, 2013

(65) Prior Publication Data
US 2014/0072559 A1    Mar. 13, 2014

Related U.S. Application Data

(60) Provisional application No. 61/699,053, filed on Sep. 10, 2012.

(30) Foreign Application Priority Data

Sep. 10, 2012 (FR) ..................... 12 58494

(51) Int. Cl.
| | |
|---|---|
| A61K 39/395 | (2006.01) |
| A61K 47/26 | (2006.01) |
| A61K 9/00 | (2006.01) |
| A61K 47/16 | (2006.01) |
| A61K 9/08 | (2006.01) |
| C07K 16/22 | (2006.01) |
| C07K 16/24 | (2006.01) |
| C07K 16/32 | (2006.01) |
| A61K 39/00 | (2006.01) |

(52) U.S. Cl.
CPC ............. *A61K 47/26* (2013.01); *A61K 9/0019* (2013.01); *A61K 9/08* (2013.01); *A61K 39/00* (2013.01); *A61K 39/395* (2013.01); *A61K 39/39591* (2013.01); *A61K 47/16* (2013.01); *C07K 16/22* (2013.01); *C07K 16/241* (2013.01); *C07K 16/32* (2013.01); *A61K 2039/505* (2013.01)

(58) Field of Classification Search
None
See application file for complete search history.

(56) References Cited

U.S. PATENT DOCUMENTS

| | | | |
|---|---|---|---|
| 6,875,751 B2 * | 4/2005 | Imbach et al. ............... | 514/49 |
| 7,666,413 B2 | 2/2010 | Liu et al. | |
| 2002/0045571 A1 | 4/2002 | Liu et al. | |

FOREIGN PATENT DOCUMENTS

| | | |
|---|---|---|
| EP | 0 125 023 A1 | 11/1984 |
| EP | 0 173 494 A3 | 3/1986 |
| WO | WO 2010/132047 A1 | 11/2010 |
| WO | WO 2011/121560 A2 | 10/2011 |
| WO | WO 2011/139718 A1 | 11/2011 |

OTHER PUBLICATIONS

"Annex 1—Summary of Product Characteristics," Sep. 17, 2009, XP002696436, pp. 1-60, http://www.ema.europa.edu/docs/en_GB/docment_library/EPAR_-_Product_Information/human/000582/WC00029271.pdf.
"An Introduction to Clinical Pharmaceuticals," *Pharmaceutical Press*, 2010, XP002696437, pp. 73-74.
Shire, "Formulation and Manufacturability of Biologics," *Current Opinion in Biotechnology*, 2009, vol. 20, pp. 708-714.
Saluja et al., "Nature and Consequences of Protein-Protein Interactions in High Protein Concentration Solutions," *International Journal of Pharmaceutics*, 2008, vol. 358, pp. 1-15.
Shire et al., "Challenges in the Development of High Protein Concentration Formulations," *Journal of Pharmaceutical Sciences*, Jun. 2004, vol. 93, No. 6, pp. 1390-1402.
Guo et al., "Structure-Activity Relationship for Hydrophobic Salts as Viscosity-Lowering Excipients for Concentrated Solutions of Monoclonal Antibodies," *Pharm. Res.*, 2012, vol. 29, No. 11, pp. 3102-3109.
Du et al., "Hydrophobic Salts Markedly Diminish Viscosity of Concentrated Protein Solutions," *Biotechnology and Bioengineering*, Mar. 2011, vol. 108, No. 3, pp. 632-636.
Frokjaer et al., "Protein Drug Stability: A Formulation Challenge," *Nature Reviews Drug Discovery*, Apr. 2005, vol. 4, pp. 298-306.
Kabat et al., "Tabulation and Analysis of Amino Acid and Nucleic Acid Sequences of Precursors, V-Regions, C-Regions, J-Chain, T-Cell Receptors for Antigen, T-Cell Surface Antigens, $\beta_2$-Microglobulins, Major Histocompatibility Antigens, Thy-1, Complement, C-Reactive Protein, Thymopoietin, Integrins, Post-gamma Globulin, $\alpha_2$-Macroglobulins, and Other Related Proteins," *Sequences of Proteins of Immunological Interest*, Fifth Edition, 1991, pp. xv.
Morrison et al., "Chimeric Human Antibody Molecules: Mouse Antigen-Binding Domains with Human Constant Region Domains," *Proc. Natl. Acad. Sci. USA*, 1984, vol. 81, No. 21, pp. 6851-6855.
Neuberger et al., "Recombinant Antibodies Possessing Novel Effector Functions," *Nature*, Dec. 1984, vol. 312, pp. 604-608.
Vincke et al., "Introduction to Heavy Chain Antibodies and Derived Nanobodies," *Methods in Molecular Biology*, 2012, vol. 911, pp. 15-26.

(Continued)

*Primary Examiner* — Yunsoo Kim
(74) *Attorney, Agent, or Firm* — Oliff PLC

(57) ABSTRACT

In an aqueous solution, a composition includes at least one protein, including at least one antibody fragment, and at least one water-soluble viscosity-reducing agent chosen from the group consisting of cytidine, 2'-deoxycytidine, uridine, 2'-deoxyuridine, thymidine and ribothymidine, alone or as a mixture. The protein includes at least one antibody fragment being at a concentration greater than or equal to 50 mg/ml.

21 Claims, No Drawings

(56) References Cited

OTHER PUBLICATIONS

Wesolowski et al., "Single Domain Antibodies: Promising Experimental and Therapeutic Tools in Infection and Immunity," *Med. Microbiol. Immunol.*, 2009, vol. 198, pp. 157-174.
Holliger et al., "'Diabodies': Small Bivalent and Bispecific Antibody Fragments," *Proc. Natl. Acad. Sci. USA*, Jul. 1993, vol. 90, pp. 6444-6448.
Cilurzo et al., "Injectability Evaluation: An Open Issue," *AAPS PharmSciTech*, Jun. 2011, vol. 12, No. 2, pp. 604-609.
Adler, "Challenges in the Development of Prefilled Syringes for Biologics from a Formulation Scientist's Point of View," *American Pharmaceutical Review*, Feb. 2012, vol. 15, No. 1, pp. 1-11.
Newsletter of the AAPS Aggregation and Biological Consequences Focus Group, Aug. 2011, vol. 2, Issue 4, pp. 1-7.
Nov. 7, 2013 Written Opinion issued in International Application No. PCT/FR2013/052076.

* cited by examiner

HIGHLY CONCENTRATED AQUEOUS PROTEIN SOLUTION WITH REDUCED VISCOSITY

CROSS-REFERENCE TO RELATED APPLICATIONS

The present application claims priority under 35 U.S.C. 119 and 35 U.S.C. 365 to U.S. provisional Application No. 61/699,753 (filed on Sep. 9, 2012).

Monoclonal antibodies (identified hereinafter as mAbs) are a class of rapidly developing therapeutic proteins for treating serious pathological conditions, such as certain cancers, infectious diseases and autoimmune diseases. Currently, more than 30 mAbs have been approved in the United States and in Europe, and approximately 20% of the therapeutic proteins currently in development are antibodies.

Antibodies may be administered parenterally, such as intravenous (IV), subcutaneous (SC) or intramuscular (IM) injection. The SC and IM routes make it possible to reduce the cost of the treatments and improve patient comfort.

For SC and IM injections, the small volume that may be injected (0.5-2 ml) imposes the development of concentrated antibody formulations since the required doses are conventionally 100 mg to 1 g in order to achieve a therapeutic effect. At concentrations above 100 mg/ml, aqueous solutions of mAbs are often unstable and viscous, making the manufacturing steps (purification, concentration and distribution steps) difficult, as is described in the publication by Shire, Current Opinion in Biotechnology, 2009, 20, 708-714.

The problem of viscosity can also be encountered for formulations of nanobodies and of fusion proteins.

The viscosity of the formulations leads to injectability problems and makes the administration painful for the patient, as is described in the publication by Cilurzo et al., AAPS Pharm Sci Tech, 2011, 12 (2), 604-9.

This viscosity of concentrated protein formulations thus becomes a real challenge, as is described in the publication by Adler, American Pharmaceutical Review, February 2012, 15(1).

Even though the factors governing these viscosity increases are quite poorly described and identified, many publications show that the increase in viscosity of highly concentrated aqueous antibody solutions results from at least two factors: steric effects (volume exclusion) and protein-protein interactions, as is described in the publication by Satuja & Kalonia, Int J Pharm, 2008, 1-15.

However, the viscosity is the only factor that is able to be modified by the formulator. This is because, in the majority of cases, the other factors, namely the doses and the caliber of the needles, cannot be modified. Thus, the need to identify viscosity-reducing excipients that are capable of lowering the viscosity of highly concentrated protein solutions has consequently become crucial and strategic in the pharmaceutical industry.

The use of a salt such as NaCl has been described in particular in the publication by Shire et al., J Pharm Sci 2004, 1390-402 or U.S. Pat. No. 7,666,413 as making it possible to lower the viscosity of concentrated aqueous mAb solutions. However, this solution is not universal and the viscosity of many mAb formulations is not reduced or not sufficiently reduced by the addition of a salt such as NaCl, as is confirmed in the publication by Guo & al., Pharm Res, 2012, 3102-9.

Amino acids (U.S. Pat. No. 7,666,413) and amino acid derivatives (patent WO 2011/139718) have also been described as making it possible to reduce the viscosity of formulations containing an active protein of mAb type. In particular, the salt arginine hydrochloride, which is a compound commonly used in protein purification and formulation processes, see for example the publication by Frokjaer S, Nat Rev Drug Discov, 2005, 4(4), 298-306, may be considered as one of the references for assessing the lowering of viscosity.

The viscosity of mAb formulations can, in certain cases, increase because of the tendency that mAbs have to aggregate at high concentrations, as described in the publication by Florence, Pharmaceutical Press, 2010. In other cases, highly concentrated mAb formulations may be viscous without the mAbs aggregated. In other cases, the mAbs may aggregate without these highly concentrated mAb formulations being viscous. In yet other cases, highly concentrated mAb formulations in aggregated or crystalline form may have a viscosity that is lower than highly concentrated mAb formulations that are equivalent but that are in nonaggregated or noncrystalline form. Thus, increased viscosity and increased aggregation are not systematically correlated. Similarly, reduction in viscosity and reduction in aggregation are not always correlated.

Patent application WO 2011/121560 describes a method for stabilizing an antibody in a liquid environment, comprising modulation of the aggregation of said antibody by binding or masking a specific lysine of the Fc region of the antibody (Lys445 residue). This application exemplifies more particularly compositions comprising bevacizumab and a nucleotide, i.e. adenosine 5'-monophosphate (AMP), guanosine 5'-monophosphate (GMP) or adenosine 5'-triphosphate (ATP). The phosphate(s) of the nucleotides interact(s) with the Lys445 residue of the Fc region of bevacizumab, thus making it possible to stabilize the bevacizumab by reducing the aggregation of said antibody. All the compounds described or claimed carry a negatively charged chain, preferably phosphate, which will allow this interaction with the Lys445 residue of the Fc region of the antibodies. Patent application WO 2011/121560 does not cite viscosity reduction. Furthermore, it has been demonstrated by the applicant that ATP, which stabilizes a commercial formulation of bevacizumab, does not make it possible to reduce the viscosity of either bevacizumab or infliximab. On the contrary, ATP increases the viscosity of bevacizumab (+14% increase).

Surprisingly, the applicant has identified natural molecules of the family of nucleosides capable of lowering the viscosity of an aqueous solution, which is difficult to inject, of at least one protein comprising at least one antibody fragment.

According to the present invention, the terms "viscosity-reducing agent" and "viscosity-reducing compound" can be used interchangeably.

The term "nucleosides" is intended to mean natural glycosylamines consisting of a base bonded to a ribose or a deoxyribose via a glycosidic bond. Among the nucleosides are in particular cytidine, uridine, thymidine or else inosine. In cells, the nucleosides may be phosphorylated by specific kinases, allowing the formation of nucleotides which are the constituent elements of DNA and RNA.

Patent application WO 2010/132047 describes a guanosine/GMP gel composition for delivering antibodies, nucleic acids and particles. The very poor solubility of guanosine does not, however, allow it to be used in a reduced-viscosity composition.

The present invention relates to a method for reducing viscosity, consisting in adding, to the aqueous solution, which is difficult to inject, of at least one protein comprising at least one antibody fragment, at least one water-soluble viscosity-reducing agent chosen from the group consisting of cytidine, 2'-deoxycytidine, uridine, 2'-deoxyuridine, thymidine and ribothymidine, alone or as a mixture.

In one embodiment, the viscosity-reducing compound is chosen from the group consisting of cytidine, uridine and ribothymidine, alone or as a mixture.

In one embodiment, the viscosity-reducing compound is chosen from the group consisting of 2'-deoxycytidine, 2'-deoxyuridine and thymidine, alone or as a mixture.

In one embodiment, the viscosity-reducing compound is chosen from the group consisting of cytidine and 2'-deoxycytidine, alone or as a mixture.

In one embodiment, the viscosity-reducing compound is chosen from the group consisting of uridine and 2'-deoxyuridine, alone or as a mixture.

In one embodiment, the viscosity-reducing compound is chosen from the group consisting of thymidine and ribothymidine, alone or as a mixture.

In one embodiment, the viscosity-reducing compound is chosen from the group consisting of cytidine, 2'-deoxycytidine and uridine, alone or as a mixture.

In one embodiment, the viscosity-reducing compound is chosen from the group consisting of 2'-deoxyuridine, thymidine and ribothymidine, alone or as a mixture.

In one embodiment, the viscosity-reducing compound is cytidine.

In one embodiment, the viscosity-reducing compound is 2'-deoxycytidine.

In one embodiment, the viscosity-reducing compound is uridine.

In one embodiment, the viscosity-reducing compound is 2'-deoxyuridine.

In one embodiment, the viscosity-reducing compound is thymidine.

In one embodiment, the viscosity-reducing compound is ribothymidine.

All these molecules are present in biological tissues.

The term "water-soluble" is intended to mean a minimum solubility of 50 mM, or even a solubility of 250 mM, at a pH of between 5 and 8, and at 25° C.

The term "viscosity-reducing agent" or "viscosity-reducing compound" is intended to mean a compound capable, according to the invention, of reducing the viscosity of an aqueous solution, which is difficult to inject, of at least one protein comprising at least one antibody fragment, by a value of at least 10%. The techniques for measuring the viscosity are known to those skilled in the art. In particular, the viscosity is measured according to the technique described in example 2.

In one embodiment, the viscosity is lowered by a value of between 10% and 90%.

In one embodiment, the viscosity is lowered by a value of between 20% and 90%.

In one embodiment, the viscosity is lowered by a value of between 30% and 85%.

In one embodiment, the viscosity is lowered by a value of between 35% and 80%.

In one embodiment, the viscosity is lowered by a value of between 35% and 77%.

In one embodiment, the viscosity is lowered by a value of between 60% and 90%.

In one embodiment, the viscosity is lowered by a value of between 60% and 80%.

In one embodiment, the viscosity is lowered by a value of at least 15%.

The term "aqueous solution" is intended to mean a solution in which water is the main solvent. An aqueous solution may also comprise a buffer, an agent for controlling the osmolality, a surfactant, a cryoprotectant, a lyoprotectant and any pharmaceutically acceptable excipient required for the preparation of a pharmaceutical composition.

The expression "aqueous solution, which is difficult to inject, of at least one protein comprising at least one antibody fragment" is intended to mean an aqueous solution of at least one protein comprising at least one antibody fragment, the viscosity of which is at least 15 cP. It is generally accepted that such a solution, the viscosity of which is at least 15 cP, is difficult to inject subcutaneously using a needle with a caliber of at least 29 G. The applicant has adopted as limit the caliber of at least 29 G, since the latter is the upper caliber admissible for the injection comfort not to be too degraded.

The expression "protein comprising at least one antibody fragment" is so intended to mean a protein chosen from monoclonal antibodies (mAbs), polyclonal antibodies, fusion proteins, nanobodies, bispecific antibodies and antibodies coupled to cytotoxic active ingredients (ADCs).

The term "monoclonal antibody" is intended to mean a "whole antibody", an "antibody fragment" or an "antibody derivative" which has an identical and unique specificity, i.e. which recognizes only one type of epitope on a given antigen.

In one embodiment, the protein comprising at least one antibody fragment is a monoclonal antibody.

According to the present invention, an antibody can also be referred to as an immunoglobulin.

The term "whole antibody" is intended to mean an antibody composed of two identical heavy chains ("HCs") and two identical light chains ("LCs") which are linked via a disulfide bridge. Each chain consists, in the N-terminal position, of a variable region (or domain) (encoded by the rearranged genes V-J for the light chains and V-D-J for the heavy chains) which is specific for the antigen against which the antibody is directed, and, in the C-terminal position, of a constant region, consisting of a single LC domain for the light chains or of several domains for the heavy chains. Each variable region comprises three segments known as "complementarity-determining regions" ("CDRs") or "hypervariable regions", which are mainly responsible for the binding to the epitope of an antigen. The two heavy chains (H, heavy) and the two light chains (L, light) are mutually identical. The light chain is composed of 2 domains, a variable domain V and a constant domain C, which are folded independently of one another in space. They are referred to as VL and CL. The heavy chain also comprises a domain V, denoted VH, and 3 or 4 domains C, denoted CH1 to CH4. Each domain comprises approximately 110 amino acids and is structured in a comparable manner. The 2 heavy chains are linked via disulfide bridges and each heavy chain is linked to a light chain also via a disulfide bridge. The region which determines the specificity of the antibody for the antigen is borne by the variable parts, whereas the constant parts can interact with the Fc receptors of the effector cells or molecules such as complement in order to mediate various functional properties. The term "VH" refers to the variable regions of a heavy immunoglobulin chain of an antibody, including the heavy chains of an Fv, scFv, dsFv, Fab, Fab' or F(ab)' fragment. The term "VL" refers to the variable regions of a light immunoglobulin chain of an antibody, including the light chains of an Fv, scFv, dsFv, Fab, Fab' or F(ab)' fragment. The term "CDR or CDRs region" is intended to denote the hypervariable regions of the heavy and light immunoglobulin chains as defined by Kabat et al. (Kabat et al., Sequences of proteins of immunological interest, 5th edition, U.S. Department of Health and Human Services, NIH, 1991 and later editions, XV). Three heavy chain CDRs and three light chain CDRs exist. The term CDR or CDRs is used here to denote, depending on the case, one or more of these regions, or even all of these regions, which contain the majority of the amino acid residues responsible for the affine binding of the antibody to the antigen or the epitope that it recognizes. The most conserved regions of the variable domains are known as the FR (for "framework") regions or sequences, of which there are 4 (FR1 to FR4).

Antibodies are subdivided into 5 classes or isotypes: IgG, IgA, IgM, IgE and IgD, according to the structure of the constant domains of the heavy chains, i.e., respectively, $\gamma$, $\sigma$, $\mu$, $\epsilon$ and $\delta$ chains.

The IgG and IgA classes are moreover subdivided into subclasses according to, in particular, the size of the hinge regions and also the number and the position of the disulfide bridges between heavy chains.

The IgG class is subdivided into 4 subclasses, i.e. IgG1, IgG2, IgG3 and IgG4.

The IgA class is, for its part, subdivided into 2 subclasses, i.e. IgA1 and IgA2.

In one embodiment, the antibody is an IgG.
In one embodiment, the antibody is an IgA.
In one embodiment, the antibody is an IgM.
In one embodiment, the antibody is an IgE.
In one embodiment, the antibody is an IgD.
In one embodiment, the antibody is an IgG1.
In one embodiment, the antibody is an IgG2.
In one embodiment, the antibody is an IgG3.
In one embodiment, the antibody is an IgG4.
In one embodiment, the antibody is an IgA1.
In one embodiment, the antibody is an IgA2.

The term "antibody fragment" is intended to mean any functional antibody fragment, e.g. Fab (antigen-binding fragment), Fv, scFv (single-chain Fv), Fc (crystallizable fragment), F(ab')2, Fab', scFv-Fc, synthetic polypeptides containing the sequences of one or more CDRs, which generally have the same binding specificity as the antibody from which they are derived.

According to the present invention, antibody fragments of the invention may be obtained from antibodies via methods such as digestion with enzymes, for instance pepsin or papain and/or by cleavage of the disulfide bridges by chemical reduction. The enzymatic digestion of antibodies with papain generates 2 identical fragments, known as "Fab fragment" (antigen-binding fragment), and an Fc fragment (crystallizable fragment). The Fc fragment is the support of the effector functions of immunoglobulins. By digestion with pepsin, an F(ab')2 fragment is generated, in which the two Fab fragments remain linked via two disulfide bridges, and the Fc fragment is split into several peptides. The F(ab')2 fragment is formed from two Fab' fragments, linked via intercatenary disulfide bridges so as to form an F(ab')2.

Thus, since the "monoclonal antibody" according to the invention may advantageously contain one or more of these fragments, all the combinations between the fragments mentioned previously form part of the invention.

The term "antibody derivative" is intended to mean any antibody, this antibody possibly comprising one or more mutations, substitutions, deletions and/or additions of one or more amino acid residues. Such an addition, substitution or deletion may be located at any position in the molecule. When several amino acids have been added, substituted or deleted, any combination of addition, substitution or deletion may be considered, provided that the resulting antibody still has at least the advantageous properties of the antibody of the invention.

According to the invention, the "monoclonal antibody" may advantageously be a "chimeric antibody" or a "humanized antibody". The term "chimeric antibody" is intended to mean an antibody in which the variable regions of the light and heavy chains, or at least one domain or fragment of these regions, belong to a species that is different than the species to which the constant regions of the light chains and of the heavy chains belong. The term "humanized antibody" is intended to mean an antibody which mainly contains human immunoglobulin sequences. This term generally refers to a nonhuman immunoglobulin which has been modified by incorporation of human sequences or of residues found in human sequences.

The antibodies according to the invention may be formed by using the standard recombinant DNA techniques well known to those skilled in the art, for example using the techniques for constructing "chimeric" antibodies that are described, for example, in Morrison et al., Proc. Natl. Acad. Sci. U.S.A., 1984, 81 (21), pp. 6851-55, in which the recombinant DNA technology is used to replace the constant region of a heavy chain and/or the constant region of a light chain of an antibody originating from a nonhuman mammal with the corresponding regions of a human immunoglobulin. Such antibodies and the method for preparing them have also been described in patent application EP 173 494, in the document Neuberger, M. S. et al., Nature 312 (5995): 604-8 (1985), and also in document EP 125 023, for example. Methods for generating chimeric antibodies are widely available to those skilled in the art. For example, the heavy and light chains of the antibody can be expressed separately using a vector for each chain, or else can be integrated into a single vector.

By way of example, among the commercialized monoclonal antibodies, mention will be made of the following monoclonal antibodies: Muromonab-CD3 (sold under the name Orthoclone Okt3®), Abciximab (sold under the name Reopro®), Rituximab (sold under the names MabThera® and Rituxan®), Basiliximab (sold under the name Simulect®), Dadizumab (sold under the name Zenapax®), Palivizumab (sold under the name Synagis®), Infliximab (sold under the name Remicade®), Trastuzumab (sold under the name Herceptin®), Alemtuzumab (sold under the names MabCampath®, Campath-1H®), Adalimumab (sold under the name Humira®), Tositumomab-T131 (sold under the name Bexxar®), Efalihzumab (sold under the name Raptiva®), Cetuximab (sold under the name Erbitux®), Ibritumomab tiuxetan (sold under the name Zevalin®), Omalizumab (sold under the name Xolair®), Bevacizumab (sold under the name Avastin®), Natalizumab (sold under the name Tysabri®), Ranibizumab (sold under the name Lucentis®), Panitumumab (sold under the name Vectibix®), Eculizumab (sold under the name Solins®), Certolizumab pegoi (sold under the name Cimzia®), Golirrumab (sold under the name Simponi®), Canakinumab (sold under the name Ilaris®), Catumaxomab (sold under the name Removab®), Ustekinumab (sold under the name Stelara®), Tocilizumab (sold in the names RoActemra® and Actemra®), Ofatumumab (sold under the name Arzerra®), Denosumab (sold under the name Prolia®), Belimumab (sold under the name Benlysta®), Raxibacumab (not yet sold), Ipillmumab (sold under the name Yervoy®) and Pertuzumab (sold under the name Perjeta®).

The term "polyclonal antibody" is intended to mean a mixture of "whole antibodies", a mixture of "antibody fragments" or a mixture of "antibody derivatives" which recognize various types of epitopes on a given antigen.

In one embodiment, the protein comprising at least one antibody fragment is a polyclonal antibody.

The term "fusion protein" is intended to mean a construct which contains several proteins of polypeptides of different origin. This fusion protein is encoded by a nucleic acid obtained via recombinant DNA techniques that are well known to those skilled in the art. According to the present invention, the fusion protein consists of a "monoclonal antibody" fragment as previously described and a fragment of a protein of interest.

In one embodiment, the protein comprising at least one antibody fragment is a fusion protein.

By way of example, mention will be made of the fusion protein consisting of a monoclonal antibody fragment which is the FC region of an IgG1 immunoglobulin and a fragment of a protein of interest which is the extracellular domain of the CTLA-4 (cytotoxic T-lymphocyte antigen 4) protein receptor, this fusion protein, i.e. abatacept, being sold under the name Orencia®.

By way of example, mention will also be made of the fusion protein consisting of a monoclonal antibody fragment which is the Fc region of an IgG and a fragment of a protein of interest which is the P75 fraction of the soluble receptor of TNF-alpha, this fusion protein, i.e. etanercept, being sold under the name Enbrel®.

By way of example, mention will also be made of the fusion protein consisting of a monoclonal antibody fragment which is the FC region of an IgG1 and a fragment of a protein of interest which is the extracellular portions of IL-1R1 (interleukln-1 receptor component) and of IL-1RAcP (TL-1 receptor accessory protein), this fusion protein, i.e. rilonacept, being sold under the name Arcalyst®.

By way of example, mention will also be made of the fusion protein consisting of a monoclonal antibody fragment which is the IgG1 hinge regions C(H)2 and C(H)3, and a fragment of a protein of interest which is the extracellular domain of LFA-3, this fusion protein, i.e. alefacept, being sold under the name Amevive®.

The term "nanobody" is intended to mean any single variable domain of immunoglobulin heavy chains. Nanobodies are more widely described in the publication D. Saerens and S. Muyldermans (eds.) Single Domain Antibodies: Methods and Protocols, Methods in Molecular Biology, vol. 911; and Wesolowski et al., Med Microbiol Immunol 2009, 198(3), 157-174.

In one embodiment, the protein comprising at least one antibody fragment is a nanobody.

The term "bispecific antibody" (also known as "bifunctional antibody" or "diabody") is intended to mean any immunoglobulin fragment comprising 2 sites of presentation to the antigen. Bifunctional antibodies are more widely described in the publication Hollinger et al., Proc. Natl. Acad. Sci. USA 90(4): 6444-6448 (1993).

In one embodiment, the protein comprising at least one antibody fragment is a bispecific antibody.

The expression "antibody coupled to a cytotoxic active principle" is intended to mean a "monoclonal antibody" as previously described, coupled to a cytotoxic active principle.

By way of example of a cytotoxic active principle, mention will in particular be made of vedotin.

In one embodiment, the protein comprising at least one antibody fragment is an antibody coupled to a cytotoxic active principle.

By way of example, the antibody coupled to a cytotoxic active principle is the antibody brentuximab coupled to the cytotoxic active principle vedotin. This antibody coupled to this cytotoxic active principle is sold under the name Adcetris®.

The invention also relates to a composition comprising, in an aqueous solution, at least one protein comprising at least one antibody fragment, and at least one water-soluble viscosity-reducing agent chosen from the group consisting of cytidine, 2'-deoxycytidins, uridine, 2'-deoxyurldine, thymidine and ribothymidine, alone or as a mixture The invention also relates to a pharmaceutical composition for subcutaneous (SC) administration comprising, in an aqueous solution, at least one protein comprising at least one antibody fragment, and at least one viscosity-reducing agent chosen from the group consisting of cytidine, 2'-deoxycytidine, undine, 2'-deoxyuridine, thymidine and ribothymidine, alone or as a mixture.

The invention also relates to a pharmaceutical composition for intravenous (IV) administration comprising, in an aqueous solution, at least one protein comprising at least one antibody fragment, and at least one viscosity-reducing agent chosen from the group consisting of cytidine, 2'-deoxycytidine, uridine, 2'-deoxyuridine, thymidine and ribothymidine, alone or as a mixture.

The invention also relates to a pharmaceutical composition for intramuscular (IM) administration comprising, in an aqueous solution, at least one protein comprising at least one antibody fragment, and at least one viscosity-reducing agent chosen from the group consisting of cytidine, 2'-deoxycytidine, uridine, 2'-deoxyuridine, thymidine and ribothymidine, alone or as a mixture.

In one embodiment of the composition, the viscosity-reducing compound is chosen from the group consisting of cytidine, uridine and ribothymidine, alone or as a mixture.

In one embodiment of the composition, the viscosity-reducing compound is chosen from the group consisting of 2'-deoxycytidine, 2'-deoxyuridine and thymidine, alone or as a mixture.

In one embodiment of the composition, the viscosity-reducing compound is chosen from the group consisting of cytidine and 2'-deoxycytidine, alone or as a mixture.

In one embodiment of the composition, the viscosity-reducing compound is chosen from the group consisting of uridine and 2'-deoxyuridine, alone or as a mixture.

In one embodiment of the composition, the viscosity-reducing compound is chosen from the group consisting of thymidine and ribothymidine, alone or as a mixture.

In one embodiment of the composition, the viscosity-reducing compound is chosen from the group consisting of cytidine, 2'-deoxycytidine and uridine, alone or as a mixture.

In one embodiment of the composition, the viscosity-reducing compound is chosen from the group consisting of 2'-deoxyuridine, thymidine and ribothymidine, alone or as a mixture.

In one embodiment of the composition, the viscosity-reducing compound is cytidine.

In one embodiment of the composition, the viscosity-reducing compound is 2'-deoxycytidine.

In one embodiment of the composition, the viscosity-reducing compound is uridine.

In one embodiment of the composition, the viscosity-reducing compound is 2'-deoxyuridine.

In one embodiment of the composition, the viscosity-reducing compound is thymidine.

In one embodiment of the composition, the viscosity-reducing compound is ribothymidine.

A concentration expressed in M is a concentration in mol/l.

A concentration expressed in mM is a concentration expressed in mmol/l.

In one embodiment of the composition, the concentration of protein comprising at least one antibody fragment in the final formulation is greater than or equal to 50 mg/ml.

In one embodiment of the composition, the concentration of protein comprising at least one antibody fragment in the final formulation is between 50 and 350 mg/ml.

In one embodiment of the composition, the concentration of protein comprising at least one antibody fragment in the final formulation is greater than or equal to 80 mg/ml.

In one embodiment of the composition, the concentration of protein comprising at least one antibody fragment in the final formulation is between 80 and 350 mg/ml.

In one embodiment of the composition, the concentration of protein comprising at least one antibody fragment in the final formulation is between 80 and 300 mg/ml.

In one embodiment of the composition, the concentration of protein comprising at least one antibody fragment in the final formulation is greater than or equal to 100 mg/ml.

In one embodiment of the composition, the concentration of protein comprising at least one antibody fragment in the final formulation is between 100 and 350 mg/ml.

In one embodiment of the composition, the concentration of protein comprising at least one antibody fragment in the final formulation is between 100 and 300 mg/ml.

In one embodiment of the composition, the concentration of protein comprising at least one antibody fragment in the final formulation is greater than or equal to 150 mg/ml.

In one embodiment of the composition, the concentration of protein comprising at least one antibody fragment in the final formulation is between 150 and 300 mg/ml.

In one embodiment of the composition, the concentration of protein comprising at least one antibody fragment in the final formulation is between 150 and 250 mg/ml.

In one embodiment of the composition, the concentration of protein comprising at least one antibody fragment in the final formulation is between 80 and 250 mg/ml.

In one embodiment of the composition, the concentration of protein comprising at least one antibody fragment in the final formulation is between 100 and 250 mg/ml.

In one embodiment of the composition, the concentration of protein comprising at least one antibody fragment in the final formulation is between 80 and 220 mg/ml.

In one embodiment of the composition, the concentration of protein comprising at least one antibody fragment in the final formulation is between 105 and 220 mg/ml.

In one embodiment of the composition, the concentration of protein comprising at least one antibody fragment in the final formulation is between 125 and 220 mg/ml.

In one embodiment of the composition, the concentration of protein comprising at least one antibody fragment in the final formulation is between 140 and 220 mg/ml.

In one embodiment of the composition, the concentration of protein comprising at least one antibody fragment in the final formulation is between 150 and 220 mg/ml.

In one embodiment of the composition, the concentration of viscosity-reducing agent in the final formulation is greater than or equal to 10 mM.

In one embodiment of the composition, the concentration of viscosity-reducing agent in the final formulation is between 10 and 350 mM.

In one embodiment of the composition, the final concentration of viscosity-reducing compound in the final formulation is between 50 and 350 mM.

In one embodiment of the composition, the final concentration of viscosity-reducing compound in the final formulation is between 100 and 350 mM.

In one embodiment or the composition, the final concentration of viscosity-reducing compound in the final formulation is between 50 and 300 mM.

In one embodiment of the composition, the final concentration of viscosity-reducing compound in the final formulation is between 100 and 300 mM.

In one embodiment of the composition, the final concentration of viscosity-reducing compound in the final formulation is between 50 and 250 mM.

In one embodiment of the composition, the final concentration of viscosity-reducing compound in the final formulation is between 100 and 250 mM.

In one embodiment of the composition, the final concentration of viscosity-reducing compound in the final formulation is between 50 and 200 mM.

In one embodiment of the composition, the final concentration of viscosity-reducing compound in the final formulation is between 100 and 200 mM.

In one embodiment of the composition, the protein comprising at least one antibody fragment is chosen from monoclonal antibodies (mAbs), polyclonal antibodies, fusion proteins, nanobodies, bispecific antibodies and antibodies coupled to cyotoxic active principles (ADCs).

In one embodiment of the composition, the protein comprising at least one antibody fragment is a monoclonal antibody.

In one embodiment of the composition, the monoclonal antibody is an IgG.

In one embodiment of the composition, the monoclonal antibody is an IgA.

In one embodiment of the composition, the monoclonal antibody is an IgM.

In one embodiment of the composition, the monoclonal antibody is an IgE.

In one embodiment of the composition, the monoclonal antibody is an IgD.

In one embodiment of the composition, the monoclonal antibody is an IgG1.

In one embodiment of the composition, the monoclonal antibody is an IgG2.

In one embodiment of the composition, the monoclonal antibody is an IgG3.

In one embodiment of the composition, the monoclonal antibody is an IgG4.

In one embodiment of the composition, the monoclonal antibody is an IgA1.

In one embodiment of the composition, the monoclonal antibody is an IgA2.

In one embodiment of the composition, the protein comprising at least one antibody fragment is a polyclonal antibody.

In one embodiment of the composition, the protein comprising at least one antibody fragment is a fusion protein.

In one embodiment of the composition, the protein comprising at least one antibody fragment is a nanobody.

In one embodiment of the composition, the protein comprising at least one antibody fragment is a bispecific antibody.

In one embodiment of the composition, the protein comprising at least one antibody fragment is an antibody coupled to a cytotoxic active principle.

In one embodiment of the composition, the composition also comprises a pharmaceutically acceptable acid.

In one embodiment of the composition, the acid is chosen from the group consisting of: hydrochloric acid, phosphoric acid, citric acid, acetic acid, ascorbic acid, ethylenediaminetetraacetic acid (also known as EDTA) and tartaric acid.

In one embodiment of the composition, the composition also comprises a pharmaceutically acceptable base.

In one embodiment of the composition, the base is chosen from the group consisting of the inorganic bases formed from metals, such as sodium, potassium, calcium or magnesium.

In one embodiment of the composition, the inorganic base is chosen from the group consisting of sodium hydroxide (NaOH), potassium hydroxide (KOH) and magnesium hydroxide ($Mg(OH)_2$).

Additionally, the pharmaceutically acceptable acids and/or bases include those derived from amino acids, for instance histidine, arginine or glycine.

In one embodiment of the composition, the composition also comprises a pharmaceutically acceptable inorganic salt.

In one embodiment of the composition, the salt is chosen from the group consisting of: the sodium salt, the potassium salt and tin(II) chloride.

In one embodiment of the composition, the composition also comprises a pharmaceutically acceptable buffer. These pharmaceutically acceptable buffers include those which are derived from the salts, from the acids and from the bases previously mentioned or from a combination thereof.

In one embodiment of the composition, the buffer is chosen from the group consisting of: monobasic sodium phosphate (also known as monosodium phosphate)/dibasic sodium phosphate (also known as disodium phosphate), monobasic potassium phosphate (also known as monopotassium phosphate)/dibasic sodium phosphate (also known as disodium phosphate)/sodium salt, acetic acid/sodium acetate, citric acid/sodium citrate, L-histidne hydrochloride/histidine, glycine hydrochloride/glycine.

In one embodiment of the composition, the composition also comprises a pharmaceutical diluent.

In one embodiment of the composition, the diluent is chosen from the group consisting of: sterile water for injection or bacteriostatic water for injection, a pH-buffered solution (such as a phosphate-buffered saline, for example), and a saline solution for injection (0.9% NaCl). Alternatively, the diluent may be an aqueous saline solution and/or a buffer.

In one embodiment of the composition, the composition also comprises a pharmaceutical preservative.

In one embodiment of the composition, the preservative is chosen from the group consisting of benzyl alcohol, phenol, m-cresol or povidone.

In one embodiment of the composition, the composition also comprises a surfactant.

In one embodiment of the composition, the surfactant is chosen from the group consisting of: polysorbate 20 (also known as PS20 or Tween 20), polysorbate 80 (also known as PS80 or Tween 80), pluronic F-68, the "Brj" compounds, and also alkylglucosides such as n-dodecyl-β-D-matoglucoside (DDM).

In one embodiment, the composition also comprises a pharmaceutically acceptable lyoprotectant and/or a pharmaceutically acceptable sugar.

In one embodiment of the composition, the pharmaceutically acceptable lyoprotectant or the pharmaceutically acceptable sugar is chosen from the group consisting of: α-trehalose, saccharose (also known as sucrose), maltose, mannitol, sorbitol and dextran. Alternatively, the lyoprotectants include amino acids such as histidine.

Quite particularly, the composition is an aqueous solution comprising:
at least one protein comprising at least one antibody fragment,
at least one buffer,
at least one surfactant, and
at least one diluent.

In one embodiment, the composition also comprises at least one pharmaceutically acceptable lyoprotectant or sugar.

In one embodiment, the composition also comprises an acid or a base.

Said acid or said base is in particular intended for adjusting the pH of the solution, in particular said acid is HCl and said base is NaOH.

The compounds included in the composition are pharmaceutically acceptable.

In one embodiment, the invention relates to a composition for injection, comprising at least one protein comprising at least one antibody fragment, sodium phosphate (monobasic, monohydrate), sodium phosphate (dibasic, dihydrate), sucrose, a polysorbate and at least one viscosity-reducing agent, in solution in water for injection.

In one embodiment, the invention relates to a composition for injection, comprising at least one protein comprising at least one antibody fragment, sodium phosphate (monobasic, anhydrous), sodium phosphate (dibasic, anhydrous), o,o-trehalose dihydrate, a polysorbate and at least one viscosity-reducing agent, in solution in water for injection.

The invention also relates to a process for lowering the viscosity of an aqueous solution, which is difficult to inject, of at least one protein comprising at least one antibody fragment, the concentration of which is greater than or equal to 50 mg/ml and the pH of which is between 5 and 8, by a value of at least 10%, consisting in preparing an aqueous solution comprising:
said protein comprising at least one antibody fragment at a concentration greater than or equal to 50 mg/ml, and at least
one water-soluble viscosity-reducing agent chosen from the group consisting of cytidine, 2'-deoxycytidine, uridine, 2'-deoxyuridine, thymidine and ribothymidine, alone or as a mixture.

In one embodiment of the process, the viscosity-reducing compound is chosen from the group consisting of cytidine, uridine and ribothymidine, alone or as a mixture.

In one embodiment of the process, the viscosity-reducing compound is chosen from the group consisting of 2'-deoxycytidine, 2'-deoxyuridine and thymidine, alone or as a mixture.

In one embodiment of the process, the viscosity-reducing compound is chosen from the group consisting of cytidine and 2'-deoxycytdine, alone or as a mixture.

In one embodiment of the process, the viscosity-reducing compound is chosen from the group consisting of uridine and 2'-deoxyuridine, alone or as a mixture.

In one embodiment of the process, the viscosity-reducing compound is chosen from the group consisting of thymidine and ribothymidine, alone or as a mixture.

In one embodiment of the process, the viscosity-reducing compound is chosen from the group consisting of cytidine, 2'-deoxycytidine and uridine, alone or as a mixture.

In one embodiment of the process, the viscosity-reducing compound is chosen from the group consisting of 2'-deoxyuridine, thymidine and ribothymidine, alone or as a mixture.

In one embodiment, the viscosity-reducing compound is cytidine.

In one embodiment, the viscosity-reducing compound is 2'-deoxycytidine.

In one embodiment, the viscosity-reducing compound is uridine.

In one embodiment, the viscosity-reducing compound is 2'-deoxyuridine.

In one embodiment, the viscosity-reducing compound is thymidine.

In one embodiment, the viscosity-reducing compound is ribothymidine.

In one embodiment of the process, the viscosity is lowered by a value of at least 15%.

In one embodiment of the process, the viscosity is lowered by a value of between 10% and 90%.

In one embodiment of the process, the viscosity is lowered by a value of between 20% and 90%.

In one embodiment of the process, the viscosity is lowered by a value of between 30% and 85%.

In one embodiment of the process, the viscosity is lowered by a value of between 35% and 80%.

In one embodiment of the process, the viscosity is lowered by a value of between 35% and 77%.

In one embodiment of the process, the viscosity is lowered by a value of between 60% and 90%.

In one embodiment of the process, the viscosity is lowered by a value of between 60% and 80%.

In one embodiment of the process, the concentration of protein comprising at least one antibody fragment in the final formulation is between 50 and 350 mg/ml.

In one embodiment of the process, the concentration of protein comprising at least one antibody fragment in the final formulation is greater than or equal to 80 mg/ml.

In one embodiment of the process, the concentration of protein comprising at least one antibody fragment in the final formulation is between 80 and 350 mg/ml.

In one embodiment of the process, the concentration of protein comprising at least one antibody fragment in the final formulation is greater than or equal to 100 mg/ml.

In one embodiment of the process, the concentration of protein comprising at least one antibody fragment in the final formulation is between 100 and 350 mg/ml.

In one embodiment of the process, the concentration of protein comprising at least one antibody fragment in the final formulation is between 80 and 300 mg/ml.

In one embodiment of the process, the concentration of protein comprising at least one antibody fragment in the final formulation is between 100 and 300 mg/ml.

In one embodiment of the process, the concentration of protein comprising at least one antibody fragment in the final formulation is greater than or equal to 150 mg/ml.

In one embodiment of the process, the concentration of protein comprising at least one antibody fragment in the final formulation is between 150 and 300 mg/ml.

In one embodiment of the process, the concentration of protein comprising at least one antibody fragment in the final formulation is between 150 and 250 mg/ml.

In one embodiment of the process, the concentration of protein comprising at least one antibody fragment in the final formulation is between 80 and 250 mg/ml.

In one embodiment of the process, the concentration of protein comprising at least one antibody fragment in the final formulation is between 100 and 250 mg/ml.

In one embodiment of the process, the concentration of protein comprising at least one antibody fragment in the final formulation is between 80 and 220 mg/ml.

In one embodiment of the process, the concentration of protein comprising at least one antibody fragment in the final formulation is between 105 and 220 mg/ml.

In one embodiment of the process, the concentration of protein comprising at least one antibody fragment in the final formulation is between 125 and 220 mg/ml.

In one embodiment of the process, the concentration of protein comprising at least one antibody fragment in the final formulation is between 140 and 220 mg/ml.

In one embodiment of the process, the concentration of protein comprising at least one antibody fragment in the final formulation is between 150 and 220 mg/ml.

In one embodiment of the process, said protein comprising at least one antibody fragment is present in the final formulation at a concentration greater than or equal to 50 mg/ml, and the viscosity is lowered by a value of at least 15% relative to the viscosity of an aqueous solution, which is difficult to Inject, of at least one protein comprising at least one antibody fragment, having the same concentration and the same pH, which does not contain said viscosity-reducing agent.

In one embodiment of the process, said protein comprising at least one antibody fragment is present in the final formulation at a concentration between 50 and 350 mg/ml, and the viscosity is lowered by a value of at least 15% relative to the viscosity of an aqueous solution, which is difficult to inject, of at least one protein comprising at least one antibody fragment, having the same concentration and the same pH, which does not contain said viscosity-reducing agent.

In one embodiment of the process, said protein comprising at least one antibody fragment is present in the final formulation at a concentration greater than or equal to 100 mg/ml, and the viscosity is lowered by a value of at least 25% relative to the viscosity of an aqueous solution, which is difficult to inject, of at least one protein comprising at least one antibody fragment, having the same concentration and the same pH, which does not contain said viscosity-reducing agent.

In one embodiment of the process, said protein comprising at least one antibody fragment is present in the final formulation at a concentration between 100 and 350 mg/ml, and the viscosity is lowered by a value of at least 25% relative to the viscosity of an aqueous solution, which is difficult to inject, of at least one protein comprising at least one antibody fragment, having the same concentration and the same pH, which does not contain said viscosity-reducing agent.

In one embodiment of the process, said protein comprising at least one antibody fragment is present in the final formulation at a concentration greater than or equal to 150 mg/ml, and the viscosity is lowered by a value of at least 35% relative to the viscosity of an aqueous solution, which is difficult to inject, of at least one protein comprising at least one antibody fragment, having the same concentration and the same pH, which does not contain said viscosity-reducing agent.

In one embodiment of the process, said protein comprising at least one antibody fragment is present in the final formulation at a concentration between 150 and 350 mg/ml, and the viscosity is lowered by a value of at least 35% relative to the viscosity of an aqueous solution, which is difficult to inject, of at least one protein comprising at least one antibody fragment, having the same concentration and the same pH, which does not contain said viscosity-reducing agent.

In one embodiment of the process, said protein comprising at least one antibody fragment is present in the final formulation at a concentration greater than or equal to 200 mg/ml, and the viscosity is lowered by a value of at least 40% relative to the viscosity of an aqueous solution, which is difficult to inject, of at least one protein comprising at least one antibody fragment, having the same concentration and the same pH, which does not contain said viscosity-reducing agent.

In one embodiment of the process, said protein comprising at least one antibody fragment is present in the final formulation at a concentration between 200 and 350 mg/ml, and the viscosity is lowered by a value of at least 40% relative to the viscosity of an aqueous solution, which is difficult to inject, of at least one protein comprising at least one antibody fragment, having the same concentration and the same pH, which does not contain said viscosity-reducing agent.

In one embodiment of the process, the viscosity, of at least 15 cP, of an aqueous solution, which is difficult to inject, of at least one protein comprising at least one antibody fragment is lowered by a value of at least 10% by said viscosity-reducing agent.

In one embodiment of the process, the viscosity, of at least 50 cP, of an aqueous solution, which is difficult to inject, of at least one protein comprising at least one antibody fragment is lowered by a value of at least 15% by said viscosity-reducing agent.

In one embodiment of the process, the viscosity, of at least 100 cP, of an aqueous solution, which is difficult to inject, of at least one protein comprising at least one antibody fragment is lowered by a value of at least 20% by said viscosity-reducing agent.

In one embodiment of the process, the viscosity, of at least 150 cP, of an aqueous solution, which is difficult to inject, of at least one protein comprising at least one antibody fragment s lowered by a value of at least 25% by said viscosity-reducing agent.

In one embodiment of the process, the viscosity, of at least 200 cP, of an aqueous solution, which is difficult to inject, of at least one protein comprising at least one antibody fragment is lowered by a value of at least 35% by said viscosity-reducing agent.

In one embodiment of the process, the concentration of viscosity-reducing agent in the final formulation is greater than or equal to 10 mM.

In one embodiment of the process, the concentration of viscosity-reducing agent in the final formulation is between 10 and 350 mM.

In one embodiment of the process, the final concentration of viscosity-reducing compound in the final formulation is between 50 and 350 mM.

In one embodiment of the process, the final concentration of viscosity-reducing compound in the final formulation is between 100 and 350 mM.

In one embodiment of the process, the final concentration of viscosity-reducing compound in the final formulation is between 50 and 300 mM.

In one embodiment of the process, the final concentration of viscosity-reducing compound in the final formulation is between 100 and 300 mM.

In one embodiment of the process, the final concentration of viscosity-reducing compound in the final formulation is between 50 and 250 mM.

In one embodiment of the process, the final concentration of viscosity-reducing compound in the final formulation is between 100 and 250 mM.

In one embodiment of the process, the final concentration of viscosity-reducing compound in the final formulation is between 50 and 200 mM.

In one embodiment of the process, the final concentration of viscosity-reducing compound in the final formulation is between 100 and 200 mM.

In one embodiment of the process, the pH of the aqueous solution, which is difficult to inject, of at least one protein comprising at least one antibody fragment is between 5 and 8.

In one embodiment of the process, the pH of the aqueous solution, which is difficult to inject, of at least one protein comprising at least one antibody fragment is between 5 and 6.5.

In one embodiment of the process, the pH of the aqueous solution, which is difficult to inject, of at least one protein comprising at least one antibody fragment is between 5.5 and 6.5.

In one embodiment of the process, the pH of the aqueous solution, which is difficult to inject, of at least one protein comprising at least one antibody fragment is between 6 and 8.

In one embodiment of the process, the pH of the aqueous solution, which is difficult to inject, of at least one protein comprising at least one antibody fragment is between 6 and 7.5.

In one embodiment of the process, the pH of the aqueous solution, which is difficult to inject, of at least one protein comprising at least one antibody fragment is between 6 and 7.

In one embodiment of the process, the protein comprising at least one antibody fragment is chosen from monoclonal antibodies (mAbs), polyclonal antibodies, fusion proteins, nanobodies, bispecific antibodies and antibodies coupled to cytotoxic active principles (ADCs).

In one embodiment, the protein comprising at least one antibody fragment is a monoclonal antibody.

In one embodiment of the process, the monoclonal antibody is an IgG.

In one embodiment of the process, the monoclonal antibody is an IgA.

In one embodiment of the process, the monoclonal antibody is an IgM.

In one embodiment of the process, the monoclonal antibody is an IgE.

In one embodiment of the process, the monoclonal antibody is an IgE.

In one embodiment of the process, the monoclonal antibody is an Ig1.

In one embodiment of the process, the monoclonal antibody is an IgG2.

In one embodiment of the process, the monoclonal antibody is an IgG3.

In one embodiment of the process, the monoclonal antibody is an IgG4.

In one embodiment of the process, the monoclonal antibody is an IgA1.

In one embodiment of the process, the monoclonal antibody is an IgA2.

In one embodiment of the process, the protein comprising at least one antibody fragment is a polyclonal antibody.

In one embodiment of the process, the protein comprising at least one antibody fragment is a fusion protein.

In one embodiment of the process, the protein comprising at least one antibody fragment is a nanobody.

In one embodiment of the process, the protein comprising at least one antibody fragment is a bispecific antibody.

In one embodiment of the process, the protein comprising at least one antibody fragment is an antibody coupled to a cytotoxic active principle.

In one embodiment of the process, the process consists in mixing an aqueous solution containing the viscosity-reducing agent(s) with an aqueous solution containing the protein comprising at least one antibody fragment.

In one embodiment of the process, the process consists in dissolving a lyophilisate containing the protein comprising at least one antibody fragment and the viscosity-reducing agent(s) using an aqueous solution.

In one embodiment of the process, the process consists in dissolving a lyophilisate containing the protein comprising at least one antibody fragment and/or the viscosity-reducing agent(s) using an aqueous solution containing the protein comprising at least one antibody fragment and/or the viscosity-reducing agent(s).

In one embodiment of the process, the process consists in preparing a mixture from an aqueous solution containing the protein comprising at least one antibody fragment and from an aqueous solution containing the viscosity-reducing agent(s), followed by concentrating this mixture, by diafiltration/ultrafiltration, or else by lyophilization and taking up the lyophilisate using an aqueous solution optionally containing the viscosity-reducing agent(s) and the volume of which is less than that of the mixture of origin, so as to obtain a solution of which the protein concentration is greater than the protein concentration of the starting protein solution.

The invention also relates to the use of at least one water-soluble viscosity-reducing agent chosen from the group consisting of cytidine, 2'-deoxycytidine, uridine, 2'-deoxyuridine, thymidine and ribothymidine, alone or as a mixture at a concentration in the final formulation of greater than or equal to 10 mM, for lowering the viscosity of an aqueous solution, which is difficult to inject, of at least one protein comprising at least one antibody fragment, the concentration of which is greater than or equal to 50 mg/ml, and the pH of which is between 5 and 8, by a value of at least 10% relative to the viscosity of an aqueous solution, which is difficult to inject, of at least one protein comprising at least one antibody fragment, having the same concentration and the same pH, which does not contain said viscosity-reducing agent.

In one embodiment of the use, the viscosity-reducing compound is chosen from the group consisting of cytidine, uridine and ribothymidine, alone or as a mixture.

In one embodiment or the use, the viscosity-reducing compound is chosen from the group consisting of 2'-deoxycytidine, 2'-deoxyuridine and thymidine, alone or as a mixture.

In one embodiment of the use, the viscosity-reducing compound is chosen from the group consisting of cytidine and 2'-deoxycytidine, alone or as a mixture.

In one embodiment of the use, the viscosity-reducing compound is chosen from the group consisting of uridine and 2'-deoxyuridine, alone or as a mixture.

In one embodiment of the use, the viscosity-reducing compound is chosen from the group consisting of thymidine and ribothymidine, alone or as a mixture.

In one embodiment of the use, the viscosity-reducing compound is chosen from the group consisting of cytidine, 2'-deoxycytidine and uridine, alone or as a mixture.

In one embodiment of the use, the viscosity-reducing compound is chosen from the group consisting of 2'-deoxyuridine, thymidine and ribothymidine, alone or as a mixture.

In one embodiment of the use, the viscosity-reducing compound is cytidine.

In one embodiment of the use, the viscosity-reducing compound is 2'-deoxycytidine.

In one embodiment of the use, the viscosity-reducing compound is uridine.

In one embodiment of the use, the viscosity-reducing compound is 2'-deoxyuridine.

In one embodiment of the use, the viscosity-reducing compound is thymidine.

In one embodiment of the use, the viscosity-reducing compound is ribothymidine.

In one embodiment of the use, the viscosity is lowered by a value of at least 15%.

In one embodiment of the use, the viscosity is lowered by a value of between 10% and 90%.

In one embodiment of the use, the viscosity is lowered by a value of between 20% and 90%.

In one embodiment of the use, the viscosity is lowered by a value of between 30% and 85%.

In one embodiment of the use, the viscosity is lowered by a value of between 35% and 80%.

In one embodiment of the use, the viscosity is lowered by a value of between 35% and 77%.

In one embodiment of the use, the viscosity is lowered by a value of between 60% and 90%.

In one embodiment of the use, the viscosity is lowered by a value of between 60% and 80%.

In one embodiment of the use, the concentration of protein comprising at least one antibody fragment in the final formulation is between 50 and 350 mg/ml.

In one embodiment of the use, the concentration of protein comprising at least one antibody fragment in the final formulation is greater than or equal to 80 mg/ml.

In one embodiment of the use, the concentration of protein comprising at least one antibody fragment in the final formulation is between 80 and 350 mg/ml.

In one embodiment of the use, the concentration of protein comprising at least one antibody fragment in the final formulation is greater than or equal to 100 mg/ml.

In one embodiment of the use, the concentration of protein comprising at least one antibody fragment in the final formulation is between 100 and 350 mg/ml.

In one embodiment of the use, the concentration of protein comprising at least one antibody fragment in the final formulation is between 80 and 300 mg/ml.

In one embodiment of the use, the concentration of protein comprising at least one antibody fragment in the final formulation is between 100 and 300 mg/ml.

In one embodiment of the use, the concentration of protein comprising at least one antibody fragment in the final formulation is greater than or equal to 150 mg/ml.

In one embodiment of the use, the concentration of protein comprising at least one antibody fragment in the final formulation is between 150 and 300 mg/ml.

In one embodiment of the use, the concentration of protein comprising at least one antibody fragment in the final formulation is between 150 and 250 mg/ml.

In one embodiment of the use, the concentration of protein comprising at least one antibody fragment in the final formulation is between 80 and 250 mg/ml.

In one embodiment of the use, the concentration of protein comprising at least one antibody fragment in the final formulation is between 100 and 250 mg/m.

In one embodiment of the use, the concentration of protein comprising at least one antibody fragment in the final formulation is between 80 and 220 mg/ml.

In one embodiment of the use, the concentration of protein comprising at least one antibody fragment in the final formulation is between 105 and 220 mg/ml.

In one embodiment of the use, the concentration of protein comprising at least one antibody fragment in the final formulation is between 125 and 220 mg/ml.

In one embodiment of the use, the concentration of protein comprising at least one antibody fragment in the final formulation is between 140 and 220 mg/ml.

In one embodiment of the use, the concentration of protein comprising at least one antibody fragment in the final formulation is between 150 and 220 mg/ml.

In one embodiment of the use, said protein comprising at least one antibody fragment is present in the final formulation at a concentration greater than or equal to 50 mg/ml, and the viscosity is lowered by a value of at least 15% relative to the viscosity of an aqueous solution, which is difficult to inject, of at least one protein comprising at least one antibody fragment, having the same concentration and the same pH, which does not contain said viscosity-reducing agent.

In one embodiment of the use, said protein comprising at least one antibody fragment is present in the final formulation at a concentration between 50 and 350 mg/ml, and the viscosity is lowered by a value of at least 15% relative to the viscosity of an aqueous solution, which is difficult to inject, of at least one protein comprising at least one antibody fragment, having the same concentration and the same pH, which does not contain said viscosity-reducing agent.

In one embodiment of the use, said protein comprising at least one antibody fragment is present in the final formulation at a concentration greater than or equal to 100 mg/ml, and the viscosity is lowered by a value of at least 25% relative to the viscosity of an aqueous solution, which is difficult to inject, of at least one protein comprising at least one antibody fragment, having the same concentration and the same pH, which does not contain said viscosity-reducing agent.

In one embodiment of the use, said protein comprising at least one antibody fragment is present in the final formulation at a concentration between 100 and 350 mg/ml, and the viscosity is lowered by a value of at least 25% relative to the viscosity of an aqueous solution, which is difficult to inject, of at least one protein comprising at least one antibody fragment, having the same concentration and the same pH, which does not contain said viscosity-reducing agent.

In one embodiment of the use, said protein comprising at least one antibody fragment is present in the final formulation at a concentration greater than or equal to 150 mg/ml, and the viscosity is lowered by a value of at least 35% relative to the viscosity of an aqueous solution, which is difficult to inject, of at least one protein comprising at least one antibody fragment, having the same concentration and the same pH, which does not contain said viscosity-reducing agent.

In one embodiment of the use, said protein comprising at least one antibody fragment is present in the final formulation at a concentration between 150 and 350 mg/ml, and the viscosity is lowered by a value of at least 35% relative to the viscosity of an aqueous solution, which is difficult to inject, of at least one protein comprising at least one antibody fragment, having the same concentration and the same pH, which does not contain said viscosity-reducing agent.

In one embodiment of the use, said protein comprising at least one antibody fragment is present in the final formulation at a concentration greater than or equal to 200 mg/ml, and the viscosity is lowered by a value of at least 40% relative to the viscosity of an aqueous solution, which is difficult to inject, of at least one protein comprising at least one antibody fragment, having the same concentration and the same pH, which does not contain said viscosity-reducing agent.

In one embodiment of the use, said protein comprising at least one antibody fragment is present in the final formulation at a concentration between 200 and 350 mg/ml, and the viscosity is lowered by a value of at least 40% relative to the viscosity of an aqueous solution, which is difficult to inject, of at least one protein comprising at least one antibody fragment, having the same concentration and the same pH, which does not contain said viscosity-reducing agent.

In one embodiment of the use, the viscosity, of at least 15 cP, of an aqueous solution, which is difficult to inject, of at least one protein comprising at least one antibody fragment is lowered by a value of at least 10% by said viscosity-reducing agent.

In one embodiment of the use, the viscosity, of at least 50 cP, of an aqueous solution, which is difficult to inject, of at least one protein comprising at least one antibody fragment is lowered by a value of at least 15% by said viscosity-reducing agent.

In one embodiment of the use, the viscosity, of at least 100 cP, of an aqueous solution, which is difficult to inject, of at least one protein comprising at least one antibody fragment is lowered by a value of at least 20% by the viscosity-reducing agent.

In one embodiment of the use, the viscosity, of at least 150 cP, of an aqueous solution, which is difficult to inject, of at least one protein comprising at least one antibody fragment is lowered by a value of at least 25% by said viscosity-reducing agent.

In one embodiment of the use, the viscosity, of at least 200 cP, of an aqueous solution, which is difficult to inject, of at least one protein comprising at least one antibody fragment is lowered by a value of at least 35% by said viscosity-reducing agent.

In one embodiment of the use, the final concentration of viscosity-reducing compound in the final formulation is between 10 and 350 mM.

In one embodiment of the use, the final concentration of viscosity-reducing compound in the final formulation is between 50 and 350 mM.

In one embodiment of the use, the final concentration of viscosity-reducing compound in the final formulation is between 100 and 350 mM.

In one embodiment of the use, the final concentration of viscosity-reducing compound in the final formulation is between 50 and 300 mM.

In one embodiment of the use, the final concentration of viscosity-reducing compound in the final formulation is between 100 and 300 mM.

In one embodiment of the use, the final concentration of viscosity-reducing compound in the final formulation is between 50 and 250 mM.

In one embodiment of the use, the final concentration of viscosity-reducing compound in the final formulation is between 100 and 250 mM.

In one embodiment of the use, the final concentration of viscosity-reducing compound in the final formulation is between 50 and 200 mM.

In one embodiment of the use, the final concentration of viscosity-reducing compound in the final formulation is between 100 and 200 mM.

In one embodiment of the use, the pH of the aqueous solution, which is difficult to inject, of at least one protein comprising at least one antibody fragment is between 5 and 6.5.

In one embodiment of the use, the pH of the aqueous solution, which is difficult to inject, of at least one protein comprising at least one antibody fragment is between 5.5 and 6.5.

In one embodiment of the use, the pH of the aqueous solution, which is difficult to inject, of at least one protein comprising at least one antibody fragment is between 6 and 8.

In one embodiment of the use, the pH of the aqueous solution, which is difficult to inject, of at least one protein comprising at least one antibody fragment is between 6 and 7.5.

In one embodiment or the use, the pH of the aqueous solution, which is difficult to inject, of at least one protein comprising at least one antibody fragment is between 6 and 7.

In one embodiment of the use, the protein comprising at least one antibody fragment is chosen from monoclonal antibodies (mAbs), polyclonal antibodies, fusion proteins, nanobodies, bispecific antibodies and antibodies coupled to cytotoxic active principles (ADCs).

In one embodiment of the use, the protein comprising at least one antibody fragment is a monoclonal antibody.

In one embodiment of the use, the monoclonal antibody is an IgG.

In one embodiment of the use, the monoclonal antibody is an IgA.

In one embodiment of the use, the monoclonal antibody is an IgM.

In one embodiment of the use, the monoclonal antibody is an IgE.

In one embodiment of the use, the monoclonal antibody is an IgD.

In one embodiment of the use, the monoclonal antibody is an IgG1.

In one embodiment of the use, the monoclonal antibody is an IgG2.

In one embodiment of the use, the monoclonal antibody is an IgG3.

In one embodiment of the use, the monoclonal antibody is an IgG4.

In one embodiment of the use, the monoclonal antibody is an IgA1.

In one embodiment of the use, the monoclonal antibody is an IgA2.

In one embodiment of the use, the protein comprising at least one antibody fragment is a polyclonal antibody.

In one embodiment of the use, the protein comprising at least one antibody fragment is a fusion protein.

In one embodiment of the use, the protein comprising at least one antibody fragment is a nanobody.

In one embodiment of the use, the protein comprising at least one antibody fragment is a bispecific antibody.

In one embodiment of the use, the protein comprising at least one antibody fragment is an antibody coupled to a cytotoxic active principle.

The invention is illustrated by the following examples. These examples demonstrate the technical effect of the viscosity-reducing compounds used according to the invention and compares them with the prior art compounds.

EXAMPLE 1

Preparation of Stock Aqueous Solutions

TABLE I

| Code | Name | Structure | Supplier reference | CAS number |
|---|---|---|---|---|
| Arg | L-arginine hydrochloride salt | 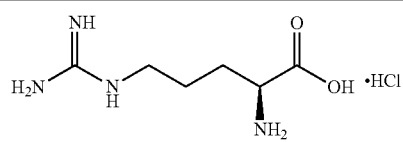 [SMILES: N=C(N)NCCC[C@H](N)C(=O)O ; Cl] | Sigma 11039 | CAS# 1119-34-2 |
| Cyt | Cytidine | 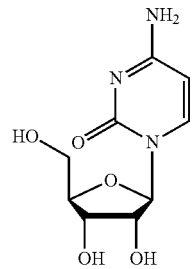 | Sigma C4654 | CAS# 65-46-3 |

TABLE I-continued

| Code | Name | Structure | Supplier reference | CAS number |
|---|---|---|---|---|
| Deoxy cyt | 2'-Deoxycytidine | (structure) | SIGMA D3897 | CAS# 951-77-9 |
| Urid | Uridine | (structure) | SIGMA U3750 | CAS# 58-96-8 |
| Deoxy urid | 2'-Deoxyuridine | (structure) | SIGMA D5412 | CAS# 951-78-0 |
| Thym | Thymidine | (structure) | SIGMA T9250 | CAS# 50-89-5 |
| Ribot hym | Ribothymidine | (structure) | SIGMA M8905 | CAS# 1463-10-1 |
| NaCl | Sodium chloride | $Na^+Cl^-$ | Cooper 171 0500 | CAS# 7647-14-5 |

TABLE I-continued

| Code | Name | Structure | Supplier reference | CAS number |
|---|---|---|---|---|
| ATP | Sodium salt of adenosine 5'-triphosphate | 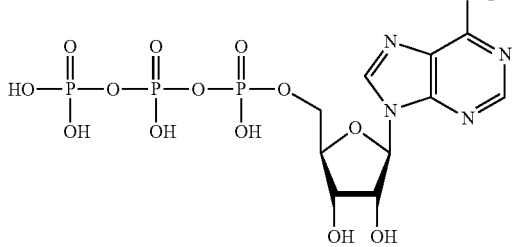 | SIGMA A3377 | CAS# 56-65-5 |

L-Arginine Hydrochloride Salt Solution

The L-arginine hydrochloride salt was obtained from Sigma-Aldrich (Sigma ref. 11039, CAS#1119-34-2) and was dissolved in Milli-Q® water while adjusting the pH between 5.5 and 8 so as to obtain a 994 mM solution of L-arginine hydrochloride salt.

Cytidine Solution

The cytidine was obtained from Sigma-Aldrich (ref. C4654, CAS#65-46-3) and was dissolved in Milli-Q® water while adjusting the pH between 5 and 8 so as to obtain a 905 mM solution of cytidine.

2'-Deoxycytidine Solution

The 2'-deoxycytidine was obtained from Sigma-Aldrich (Aldrich ref. D3897, CAS#951-77-9) and was dissolved in Milli-Q® water while adjusting the pH between 5 and 8 so as to obtain a 1120 mM solution of 2'-deoxycytidine.

Uridine Solution

The uridine was obtained from Sigma-Aldrich (Aldrich ref. U3750, CAS#58-96-8) and was dissolved in Milli-Q® water while adjusting the pH between 5 and 8 so as to obtain a 1000 mM solution of uridine.

2'-Deoxyuridine Solution

The 2'-deoxyuridine was obtained from Sigma (ref. D5412, CAS#951-78-0) and was dissolved in Milli-Q® water while adjusting the pH between 5 and 8 so as to obtain a 200 mM solution of 2'-deoxyurdine.

Thymidine Solution

The thymidine was obtained from Sigma (ref. T9250, CAS#50-89-5) and was dissolved in Milli-Q® water while adjusting the pH between 5 and 8 so as to obtain a 20 mM solution of thymidine.

Ribothymidine Solution

The ribothymidine was obtained from Sigma (ref. M8905, CAS#1463-10-1) and was dissolved in Milli-Q® water while adjusting the pH between 5 and 8 so as to obtain a 200 mM solution of ribothymidine.

Sodium Chloride Solution

The sodium chloride was obtained from Cooper (Cooper ref. 171 0500, CAS#7647-14-5) in Milli-Q® water so as to obtain a 2500 mM solution of NaCl salt.

Solution of the Sodium Salt of Adenosine 5'-Triphospate

The sodium salt of adenosine 5'-triphosphate (ATP) was obtained from Sigma (ref. A3377, CAS#56-65-5) in Milli-Q® water, with the pH being adjusted to between 5 and 8, so as to obtain a 1120 mM solution of the sodium salt of adenosine 5'-triphosphate.

EXAMPLE 2

Effect of Uridine on the Viscosity of Various Highly Concentrated Therapeutic Protein Solutions Compared with that of Arginine and NaCl This example illustrates how uridine reduces the viscosity or three formulations of monoclonal antibodies in comparison with the reference compounds, namely arginine hydrochloride and NaCl.

For this example, three solutions of monoclonal antibodies, i.e. a solution of bevacizumab (an IgG1 sold under the name Avastin® by Genentech/Hoffmann La Roche), a solution of infliximab (an IgG1/κ sold under the name Remicade® by Schering-Plough) and a solution of trastuzumab (an IgG1/κ sold under the name Herceptin® by Genentech), were concentrated by ultrafiltration on Amicon® Ultra-15 centrifuge filtration units with a cutoff threshold of 50 kDa. The protein concentration of each concentrated solution was measured by UV spectroscopy (absorbance at 280 nm) after dilution of the samples.

The commercial solution of bevacizumab (25 mg/ml) was concentrated to 268 mg/ml. For infliximab and trastuzumab, the commercial products are lyophilisates which were first of all reconstituted using water for injection to the concentration suggested by the manufacturer (i.e. 10 mg/ml for infliximab and 21 mg/ml for trastuzumab). Once reconstituted, the infliximab and trastuzumab formulations were concentrated to, respectively, 183 mg/ml and 243 mg/ml.

The pH values of the commercial formulations of therapeutic proteins used for these tests are summarized in table II below:

TABLE II

|  | bevacizumab | infliximab | trastuzumab |
|---|---|---|---|
| pH of the commercial formulation | 6.2 ± 0.2 | 7.2 ± 0.2 | 6.0 ± 0.2 |

The effect of uridine compared with that of arginine and of NaCl on the viscosity of these three highly concentrated therapeutic protein solutions was then evaluated. For this, the viscosity was measured using a cone/plate rheometer (TA Instruments, AR 2000 Ex, geometry or diameter 20 mm, cone of 0.5131°, solvent trap filled with water) at a temperature of 21° C. and in flow sweep mode with shear rates of between 5000 and 50 s$^{-1}$ (3 points per decade-steady-state sensing). All the viscosity values are determined at the level of the Newtonian plateau.

For this example, the "Protein+Urid", "Protein+Arg" and "Protein+NaCl" formulations were prepared by mixing one of the previously prepared undine, arginine or NaCl solutions, with Milli-Q® water and with one of the previously prepared concentrated protein solutions so as to achieve a final uridine, arginine or NaCl concentration of 150 mmol/l (mM) and a final protein concentration of 220 mg/ml for bevacizumab, 150 mg/ml for infliximab and 200 mg/ml for trastuzumab. The samples thus prepared were stored at ambient temperature and were analyzed using a rheometer within 24 hours of their preparation.

The "control" solutions are prepared by dilution in Milli-Q® water, so as to achieve a final protein concentration of 220 mg/ml for bevacizumab, 150 mg/ml for infliximab and 200 mg/ml for trastuzumab.

The pH of these formulations ("Protein+Urid", "Protein+Arg" and "Protein+NaCl" and "controls") is the same as that of the commercial formulation of the corresponding therapeutic protein (table II).

The results of the measurements relating to this second example are given in table III hereinafter in the form of percentages of viscosity reduction relative to the control solution of therapeutic protein alone, at the same protein concentration as the "Protein+Urid", "Protein+Arg" or "Protein+NaCl" formulations.

TABLE III

| Concentration tested | % viscosity reduction relative to the "protein alone" control | | |
|---|---|---|---|
| | bevacizumab 220 mg/ml | infliximab 150 mg/ml | trastuzumab 200 mg/ml |
| 150 mM NaCl | 24% | 6% | 34% |
| 150 mM Arg | 46% | 55% | 48% |
| 150 mM Urid | 64% | 70% | 35% |

The data given in table III demonstrate that, in the presence of 150 mM of uridine, the viscosity of the 3 highly concentrated protein solutions is significantly reduced, by 64% with bevacizumab at 220 mg/ml, by 70% with infliximab at 150 mg/ml and by 35% with trastuzumab at 200 mg/l. In addition, uridine proves to be significantly more effective than arginine and NaCl for lowering the viscosity of the highly concentrated solutions of bevacizumab and of infliximab.

EXAMPLE 3

Effect of Cytidine, of 2'-Deoxycytidine and of Uridine on the Viscosity of Two Highly Concentrated Aqueous Formulations of Monoclonal Antibodies Compared with that of Arginine, of NaCl and of the Sodium Salt of Adenosine 5'-Triphosphate This example illustrates the lowering of the viscosity of highly concentrated solutions of bevacizumab and of infliximab by cytidine, 2'-deoxycytidine and uridine in comparison with reference compounds such as arginine and NaCl and in comparison with the sodium salt of adenosine 5'-triphosphate.

In this study, the highly concentrated bevacizumab and infliximab solutions used are the same as those which were prepared and used previously. The "Protein+Cyt", "Protein+Deoxycyt", "Protein+Urid", "Protein+Arg", "Protein+NaCl" and "Protein+ATP" formulations were prepared in the presence of 150 mM of cytidine, of 2'-deoxycytidine, of uridine, of arginine, of NaCl or of sodium salt of adenosine 5'-triphosphate.

The viscosity of the "Protein+Cyt", "Protein+Deoxycyt" and "Protein+Urid" formulations was then measured as described in example 2 and compared with that obtained for the "Protein+Arg", "Protein+NaCl" and "Protein+ATP" formulations. The pH of these formulations is the same as that of the corresponding therapeutic protein formulation, i.e. 6.2±0.2 for bevacizumab and 7.2±0.2 for infliximab.

The results of the measurements relating to this example are given in tables IV and V hereinafter in the form of percentages of viscosity reduction relative to the control solution of therapeutic protein alone, at the same protein concentration as the "Protein+Cyt", "Protein+Deoxycyt", "Protein+Urid", "Protein+Arg", "Protein+NaCl" and "Protein+ATP" formulations.

TABLE IV

| | Concentration tested | % viscosity reduction relative to the "protein alone" control |
|---|---|---|
| bevacizumab 220 mg/ml | 150 mM NaCl | 24% |
| | 150 mM Arg | 46% |
| | 150 mM ATP | −14% |
| | 150 mM Cyt | 43% |
| | 150 mM Deoxycyt | 51% |
| | 150 mM Urid | 64% |

The data given in table TV demonstrate that, when used at 150 mM, cytidine, 2'-deoxycytidine and uridine reduce the viscosity of bevacizumab at 220 mg/ml significantly more effectively than NaCl at the same concentration. Moreover, 2'-deoxycytidine and uridine reduce the viscosity of bevacizumab at 220 mg/ml more effectively than arginine at the same concentration.

The sodium salt of adenosine 5'-triphosphate does not make it possible, a fortiori, to reduce the viscosity of bevacizumab. On the contrary, the sodium salt of adenosine 5'-triphosphate increases the viscosity of the latter (+14% increase).

TABLE V

| | Concentration tested | % viscosity reduction relative to the "protein alone" control |
|---|---|---|
| infliximab 150 mg/ml | 150 mM ATP | 0% |
| | 150 mM NaCl | 6% |
| | 150 mM Arg | 55% |
| | 150 mM Urid | 70% |
| | 150 mM Deoxycyt | 75% |
| | 150 mM Cyt | 76% |

The data given in table V demonstrate that, when used at 150 mM, cytidine, 2'-deoxycytidine and uridine reduce the viscosity of infliximab at 150 mg/ml significantly more effectively than NaCl and arginine at the same concentration. Cytidine, 2'-deoxycytidine and uridine are in particular more than 10 times more effective than NaCl.

The sodium salt of adenosine 5'-triphosphate does not make it possible to reduce the viscosity of infliximab.

EXAMPLE 4

Effect of the Concentration of a Monoclonal Antibody on the Lowering of Viscosity in the Presence of Cytidine Compared with that in the Presence of Arginine The objective of this example is to compare the effectiveness in viscosity reduction of cytidine with that of arginine as a function of antibody concentration.

The highly concentrated infliximab solution used is the same as that which was prepared previously. The "Protein+Cyt" and "Protein+Arg" formulations were prepared in the presence of 150 mM of cytidine or of arginine and with infliximab concentrations decreasing from 150 mg/ml to 80 mg/ml.

The pH of these formulations is the same as that of the commercial infliximab formulation, i.e. 7.2±0.2. The viscosity of the formulations thus prepared was measured as described in example 2.

The results of the measurements relating to this example are given in table VI hereinafter in the form of percentages of viscosity reduction relative to the control Infliximab solution.

TABLE VI

| Infliximab concentration | % viscosity reduction relative to the control infliximab solution | |
|---|---|---|
| (mg/ml) | Arg to 150 mM | Cyt to 150 mM |
| 80 | 36% | 58% |
| 105 | 47% | 68% |
| 125 | 46% | 69% |
| 140 | 59% | 77% |
| 150 | 55% | 76% |

The data given in table VI show that cytidine lowers the viscosity of infliximab significantly more effectively than arginine at all the infliximab concentrations tested.

EXAMPLE 5

Effect of Cytidine Concentration on the Decrease in Viscosity of a Highly Concentrated Aqueous Formulation of Monoclonal Antibody Compared with that of Arginine and of NaCl The highly concentrated infliximab solution used is the same as that which was prepared and used previously. The "Protein+Cyt", "Protein+Arg" and "Protein+NaCl" formulations were prepared in the presence of concentrations increasing from 0 to 300 mM of cytidine, arginine or NaCl.

The pH of these formulations is the same as that of the commercial infliximab formulation, i.e. 7.2 f 0.2. The viscosity of the formulations thus prepared was measured as described in example 2.

The results of the measurements relating to this example are given in table VII hereinafter in the form of percentages of viscosity reduction relative to the control solution of therapeutic protein alone, at the same protein concentration as the "Protein+Cyt", "Protein+Arg" and "Protein+NaC" formulations.

TABLE VII

| | Concentration tested | Arg % viscosity reduction relative to the "protein alone" control | Cyt % viscosity reduction relative to the "protein alone" control | NaCl % viscosity reduction relative to the "protein alone" control |
|---|---|---|---|---|
| Infliximab 105 mg/ml | 50 mM | 32% | 39% | 20% |
| | 150 mM | 46% | 68% | −6% |
| | 300 mM | 58% | 72% | −90% |

The data given in table VII show that, whatever the concentration of cytidine used, the latter is always significantly more effective than arginine and NaCl.

EXAMPLE 6

Examples of Compositions According to the Invention 6.1 Composition in the form of a highly concentrated solution of bevacizumab, the pH of which is 6.2, comprising cytidine

| Ingredient: | Concentration (mg/ml): |
|---|---|
| bevacizumab | 200 |
| Sodium phosphate (monobasic, monohydrate) | 5.8 |
| Sodium phosphate (dibasic, anhydrous) | 1.2 |
| α,α-Trehalose dehydrate | 60 |
| Polysorbate 20 | 0.4 |
| Cytidine (Cyt) | 36.5 |
| Water for injection, USP | qs | as means quantity sufficient for.

6.2 Composition in the form of a highly concentrated solution of bevacizumab, the pH of which is 6.2, comprising uridine

| Ingredient: | Concentration (mg/ml): |
|---|---|
| bevacizumab | 200 |
| Sodium phosphate (monobasic, monohydrate) | 5.8 |
| Sodium phosphate (dibasic, anhydrous) | 1.2 |
| α,α-Trehalose dehydrate | 60 |
| Polysorbate 20 | 0.4 |
| Uridine (Urid) | 36.6 |
| Water for injection, USP | qs |

6.3 Composition in the form of a highly concentrated solution of infliximab, the pH of which is 7.2, comprising uridine

| Ingredient: | Concentration (mg/ml): |
|---|---|
| Infliximab | 150 |
| Sodium phosphate (monobasic, monohydrate) | 0.22 |
| Sodium phosphate (dibasic, dihydrate) | 0.61 |
| Sucrose | 50 |
| Polysorbate 80 | 0.05 |
| Uridine (Urid) | 36.6 |
| Water for injection, USP | qs |

6.4 Composition in the form of a highly concentrated solution of infliximab, the pH of which is 7.2, comprising uridine

| Ingredient: | Concentration (mg/ml): |
|---|---|
| Infliximab | 150 |
| Sodium phosphate (monobasic, monohydrate) | 0.22 |
| Sodium phosphate (dibasic, dihydrate) | 0.61 |
| Sucrose | 50 |
| Polysorbate 80 | 0.05 |
| Cytidine (Cyt) | 36.5 |
| Water for injection, USP | qs |

6.5 Composition in the form of a highly concentrated solution of bevacizumab, the pH of which is 6.2, comprising 2'-deoxycytidine

| Ingredient: | Concentration (mg/ml): |
|---|---|
| bevacizumab | 200 |
| Sodium phosphate (monobasic, monohydrate) | 5.8 |
| Sodium phosphate (dibasic, anhydrous) | 1.2 |
| α,α-Trehalose dehydrate | 60 |
| Polysorbate 20 | 0.4 |
| 2'-Deoxycytidine (Deoxycyt) | 34.1 |
| Water for injection, USP | qs |

6.6 Composition in the form of a highly concentrated solution of Infliximab, the pH of which is 7.2, comprising 2'-deoxycytidine

| Ingredient: | Concentration (mg/ml): |
|---|---|
| Infliximab | 150 |
| Sodium phosphate (monobasic, monohydrate) | 0.22 |
| Sodium phosphate (dibasic, dihydrate) | 0.61 |
| Sucrose | 50 |
| Polysorbate 80 | 0.05 |
| 2'-Deoxycytidine (Deoxycyt) | 34.1 |
| Water for injection, USP | qs |

6.7 Composition in the form of a highly concentrated solution of bevacizumab, the pH of which is 6.2, comprising thymidine

| Ingredient: | Concentration (mg/ml): |
|---|---|
| bevacizumab | 200 |
| Sodium phosphate (monobasic, monohydrate) | 5.8 |
| Sodium phosphate (dibasic, anhydrous) | 1.2 |
| α,α-Trehalose dehydrate | 60 |
| Polysorbate 20 | 0.4 |
| Thymidine (Thym) | 36.3 |
| Water for injection, USP | qs |

6.8 Composition in the form of a highly concentrated solution of Infliximab, the pH of which is 7.2, comprising thymidine

| Ingredient: | Concentration (mg/ml): |
|---|---|
| Infliximab | 150 |
| Sodium phosphate (monobasic, monohydrate) | 0.22 |
| Sodium phosphate (dibasic, dihydrate) | 0.61 |
| Sucrose | 50 |
| Polysorbate 80 | 0.05 |
| Thymidine (Thym) | 36.3 |
| Water for injection, USP | qs |

6.9 Composition in the form of a highly concentrated solution of bevacizumab, the pH of which is 6.2, comprising ribothymidine

| Ingredient: | Concentration (mg/ml): |
|---|---|
| bevacizumab | 200 |
| Sodium phosphate (monobasic, monohydrate) | 5.8 |
| Sodium phosphate (dibasic, anhydrous) | 1.2 |
| α,α-Trehalose dehydrate | 60 |
| Polysorbate 20 | 0.4 |
| Ribothymidine | 38.7 |
| Water for injection, USP | qs |

6.10 Composition in the form of a highly concentrated solution of bevacizumab, the pH of which is 6.2, comprising 2'-deoxyuridine

| Ingredient: | Concentration (mg/ml): |
|---|---|
| bavacizumab | 200 |
| Sodium phosphate (monobasic, monohydrate) | 5.8 |
| Sodium phosphate (dibasic, anhydrous) | 1.2 |
| α,α-Trehalose dehydrate | 60 |
| Polysorbate 20 | 0.4 |
| 2'-deoxyuridine | 34.2 |
| Water for injection, USP | qs |

6.11 Composition in the form of a highly concentrated solution of infliximab, the pH of which is 7.2, comprising ribothymidine

| Ingredient: | Concentration (mg/ml): |
|---|---|
| Infliximab | 150 |
| Sodium phosphate (monobasic, monohydrate) | 0.22 |
| Sodium phosphate (dibasic, dihydrate) | 0.61 |
| Sucrose | 50 |
| Polysorbate 80 | 0.05 |
| Ribothymidine | 38.7 |
| Water for injection, USP | qs |

6.12 Composition in the form of a highly concentrated solution of infliximab, the pH of which is 7.2, comprising 2'-deoxyuridine

| Ingredient: | Concentration (mg/ml): |
|---|---|
| Infliximab | 150 |
| Sodium phosphate (monobasic, monohydrate) | 0.22 |
| Sodium phosphate (dibasic, dihydrate) | 0.61 |
| Sucrose | 50 |
| Polysorbate 80 | 0.05 |
| 2'-deoxyuridine | 34.2 |
| Water for injection, USP | qs |

What is claimed is:

1. A composition comprising, in an aqueous solution, at least one protein comprising at least one antibody fragment, and at least one water-soluble viscosity-reducing agent chosen from the group consisting of cytidine, 2'-deoxycytidine, uridine, 2'-deoxyuridine, thymidine and ribothymidine, alone or as a mixture.

2. The composition as claimed in claim 1, wherein the viscosity-reducing agent is chosen from cytidine, 2'-deoxycytidine and uridine, alone or as a mixture.

3. The composition as claimed in claim 1, wherein the concentration of protein comprising at least one antibody fragment in the final formulation is greater than or equal to 50 mg/ml.

4. The composition as claimed in claim 1, wherein the concentration of protein comprising at least one antibody fragment in the final formulation is between 50 and 350 mg/ml.

5. The composition as claimed in claim 1, wherein the concentration of protein comprising at least one antibody fragment in the final formulation is between 100 and 350 mg/ml.

6. The composition as claimed in claim 1, wherein its pH is between 5 and 8.

7. The composition as claimed in claim 1, wherein the concentration of viscosity-reducing agent is greater than or equal to 10 mM.

8. The composition as claimed in claim 1, wherein the final concentration of viscosity-reducing compound is between 10 and 350 mM.

9. The composition as claimed in claim 1, wherein the final concentration of viscosity-reducing compound is between 50 and 350 mM.

10. The composition as claimed in claim 1, wherein the protein comprising at least one antibody fragment is chosen from monoclonal antibodies, polyclonal antibodies, fusion proteins, nanobodies, bispecific antibodies and antibodies coupled to cytotoxic active principles (ADCs).

11. The composition as claimed in claim 1, wherein the protein comprising at least one antibody fragment is a monoclonal antibody.

12. The composition as claimed in claim 1, wherein the protein comprising at least one antibody fragment is a fusion protein.

13. The composition as claimed in claim 1, wherein the protein comprising at least one antibody fragment is a nanobody.

14. The composition as claimed in claim 1, wherein the protein comprising at least one antibody fragment is a bispecific antibody.

15. The composition as claimed in claim 1, wherein the protein comprising at least one antibody fragment is a bifunctional antibody.

16. The composition as claimed in claim 1, wherein the protein comprising at least one antibody fragment is an antibody coupled to a cytotoxic active principle.

17. The composition as claimed in claim 1, which is an aqueous solution comprising:

at least one protein comprising at least one antibody fragment,
at least one buffer,
at least one surfactant, and
at least one diluent.

18. A process for lowering the viscosity of an aqueous solution, which is difficult to inject, of at least one protein comprising at least one antibody fragment, the concentration of which is greater than or equal to 50 mg/ml and the pH of which is between 5 and 8, by a value of at least 10% relative to the viscosity of an aqueous solution of at least one protein comprising at least one antibody fragment, having the same concentration and the same pH, which does not contain said viscosity-reducing agent, consisting in preparing an aqueous solution comprising:

said protein of interest comprising at least one antibody fragment at a concentration greater than or equal to 50 mg/ml, and
a water-soluble viscosity-reducing agent chosen from the group consisting of cytidine, 2'-deoxycytidine, uridine, 2'-deoxyuridine, thymidine and ribothymidine, alone or as a mixture.

19. A pharmaceutical composition for parenteral administration, comprising, in an aqueous solution, at least one protein comprising at least one antibody fragment, and at least one viscosity-reducing agent chosen from the group consisting of cytidine, 2'-deoxycytidine, uridine, 2'-deoxyuridine, thymidine and ribothymidine, alone or as a mixture.

20. A pharmaceutical composition for subcutaneous (SC) administration comprising, in an aqueous solution, at least one protein comprising at least one antibody fragment, and at least one viscosity-reducing agent chosen from the group consisting of cytidine, 2'-deoxycytidine, uridine, 2'-deoxyuridine, thymidine and ribothymidine, alone or as a mixture.

21. A pharmaceutical composition for intramuscular (IM) administration comprising, in an aqueous solution, at least one protein comprising at least one antibody fragment, and at least one viscosity-reducing agent chosen from the group consisting of cytidine, 2'-deoxycytidine, uridine, 2'-deoxyuridine, thymidine and ribothymidine, alone or as a mixture.

* * * * *